United States Patent
Grillo

[11] Patent Number: 5,261,420
[45] Date of Patent: Nov. 16, 1993

[54] SUPPORT PILLOW

[76] Inventor: Josephine M. Grillo, 2111 Scenic Bay Dr., Arlington, Tex. 76013

[21] Appl. No.: 901,808

[22] Filed: Jun. 22, 1992

[51] Int. Cl.$^5$ ................. A61G 15/00; A41D 13/00
[52] U.S. Cl. .......................................... 128/845; 2/2
[58] Field of Search ................. 602/17, 18; 2/16, 45, 2/414, 415, 44; 128/845; 5/636, 637

[56] References Cited

U.S. PATENT DOCUMENTS

| | | | |
|---|---|---|---|
| 3,233,248 | 2/1966 | Bushnell | 2/2 |
| 3,496,928 | 2/1970 | Piccolo | 128/845 |
| 3,497,872 | 3/1970 | Mitchell | 2/2 |
| 3,550,159 | 12/1970 | Alarco | 2/2 |
| 3,608,964 | 9/1971 | Earl | 297/397 |
| 3,828,377 | 8/1974 | Fary, Sr. | 5/327 B |
| 4,232,663 | 11/1980 | Newton | 602/18 |
| 4,235,472 | 11/1980 | Sparks | 5/637 |
| 4,401,111 | 8/1983 | Blackstone | 602/18 |
| 4,441,221 | 4/1984 | Enste et al. | 5/431 |
| 4,453,540 | 6/1984 | Frain | 128/134 |
| 4,501,023 | 2/1985 | Bilberry | 2/2 |
| 4,538,597 | 9/1985 | Lerman | 602/18 |
| 4,733,482 | 6/1988 | Warren | 297/458 |
| 4,866,789 | 9/1989 | Dorn | 2/2 |
| 4,924,103 | 5/1990 | Stein | 2/2 |

Primary Examiner—Michael A. Brown
Attorney, Agent, or Firm—Richards, Medlock & Andrews

[57] ABSTRACT

A support pillow for severely disabled persons to maintain them in an erect posture. The support pillow comprises a planar frontal element to rest beside the patient's chest, the top of which has a portion defining a chin support area having a lower mid-point than the outer ends of the chin rest, and adjacent to the chin rest and extending rearward is at least one neck support element. This neck support element is of sufficient length to extend beyond the patient's neck, thus providing lateral support to the patient's neck such that in combination with the chin rest, the patient's head is held in a substantially normal attitude.

18 Claims, 3 Drawing Sheets

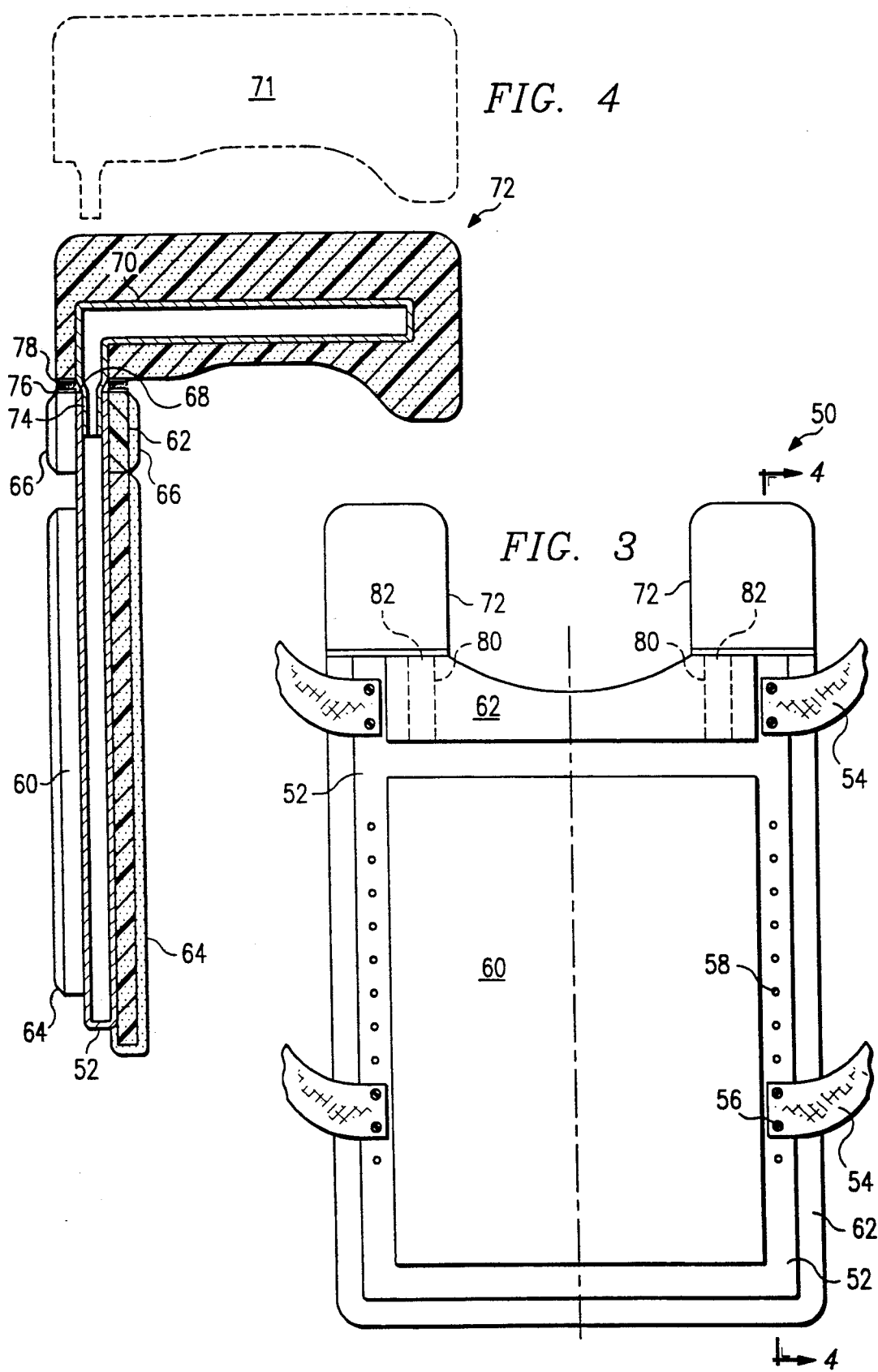

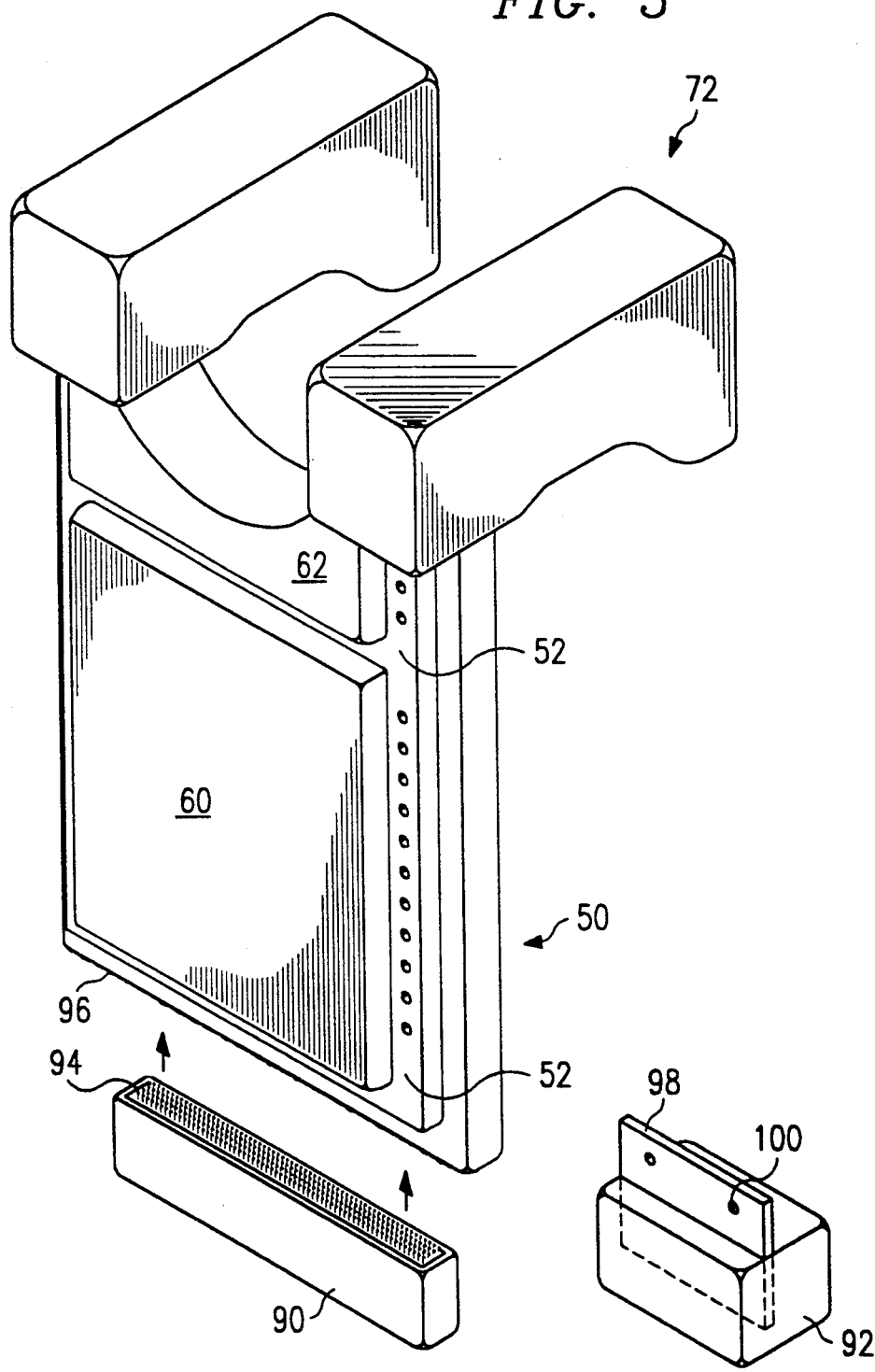

SUPPORT PILLOW

TECHNICAL FIELD OF THE INVENTION

The present invention relates to medical devices, and in particular, a therapeutic support for severely disabled individuals.

BACKGROUND OF THE INVENTION

Many patients cannot control their head and neck muscles, and thus, cannot sit upright with their head maintained at a normal attitude. Such patients may be victims of muscular dystrophy scoliosis, cerebral palsy, aging, stroke or by other diseases or injuries, becoming paraplegic or quadriplegic. Many of these patients in nursing home situations are either allowed to lay in bed endlessly or are positioned in wheelchairs with a reclined back such that they are looking at the ceiling. Such a position can cause chronic respiratory problems in these patients because it allows saliva and mucus to drain into the throat. Such drainage can even contribute to pneumonia. Also, a common practice in many nursing homes and care facilities has been to strap the patient to a wheelchair with a cloth harness, which does not support either the head or neck and does not give the patient normal posture, but rather has them suspended in a slouch, which is not conducive to the proper functioning of organs nor, in the case of children, the proper growth of bone structure.

While numerous support systems for use with wheelchairs are available, they are typically highly specific in nature and very expensive. Further, such systems provide no support for the patient while sitting in bed or during other activities.

SUMMARY OF THE INVENTION

The present invention provides a supportive pillow system which assists the patient in maintaining proper sitting posture and also maintains the head in a normal attitude. In one aspect, the support pillow of the present invention comprises a substantially planar front section with a width at the top approximately shoulder width and having a mid-section which is a recessed chin support, with the remainder of the front being any desired shape. Extending from the top of the front section is at least one neck support member which extends rearward from the planar front section. The neck support member is of sufficient height and shape that when the pillow is in position, the bottom of the neck support member can rest along the patient's shoulder. The height of the neck support member may be preferably at a height which is slightly below the level of the user's ear. In one embodiment, the invention may be made from a unitary structure such as foamed plastic. In another aspect, the invention relates to a support pillow having an internal unitary frame disposed over which is foamed plastic to provide a pliable, resilient pillow. Again, the pillow has a substantially planar front section, the top portion of which is sufficient to stretch across the shoulders of the user with a chin rest interposed in between and one or two neck support members extending rearward from the top of the planar front. The remainder of the front may be of any desired shape and the neck support members may also be of any desired shape. In an alternate embodiment, the neck support members are rectangular with a bottom section curved such that they hook over the shoulders. The pillow can be provided with one or more straps to secure the pillow and patient to a wheelchair, for example, or to secure the support pillow to the patient when the patient is sitting in bed, for example.

In another aspect, the pillow can be made in multiple pieces, wherein there is a substantially planar front portion which is adapted at the top to attach one or more shoulder support members. Means for attaching the shoulder support members is provided at the top of the front section. Preferably, such attachment means is releasable. Further, the pillow would have a multiple means available for attaching one or more straps so as to allow the pillow to be configured to the needs of the individual user. In the preferred embodiment, means for connecting extensions to the front section of the pillow are provided at the bottom of the pillow. Again, preferably the means for connecting extensions are releasable mechanisms.

BRIEF DESCRIPTION OF THE DRAWINGS

The present invention will be more clearly understood with reference to the drawings and to the detailed description. The drawings are as follows:

FIG. 3 is a frontal view of another embodiment of the present invention;

FIG. 4 is a cross-sectional view of FIG. 3 along line 4—4 of FIG. 3.

FIG. 5 is an isometric view of yet another embodiment of the present invention.

DETAILED DESCRIPTION

Figure 1:
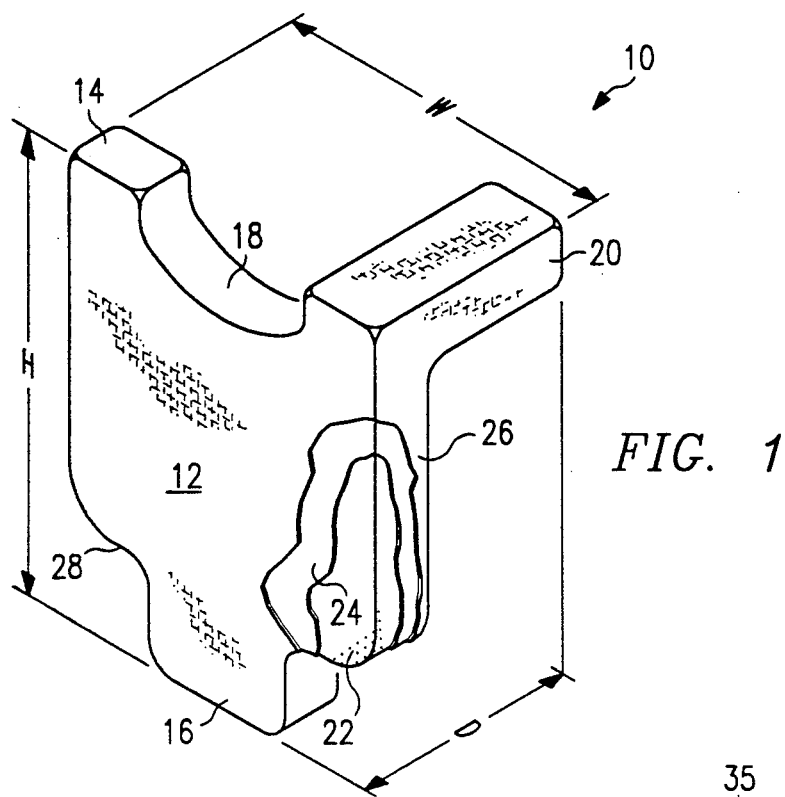
FIG. 1 is an isometric view of one embodiment of the present invention.

FIG. 1 shows an isometric view of one embodiment of the present invention. A unitary support pillow 10 has a substantially planar frontal section 12. The planar frontal section has a top surface 14 and a bottom surface 16. Bottom surface may be of any desired configuration. It may be flat or have an irregular shape, as shown in FIG. 1. For ease of convenience, we will refer to the width as the dimension indicated along axis W in FIG. 1, height as indicated along axis H in FIG. 1, and depth to indicate the distance from the front of the pillow rearward along axis D in FIG. 1. These terms will be used in a similar manner for each figure.

About midway in the top 14 of the planar frontal portion is chin support 18. Chin support 18 is preferably of a shape where the center portion is lower in height than the outer portions and is a smoothly curved surface for support of the patient's chin. On either side of this chin support, extending from the top of the substantially planar front, is a neck support element 20. As shown, there is one neck support element; however, two neck support elements may extend rearward from the front section if desired, as shown in other figures. If one section is used, it may extend from either side, depending on the patient's needs.

The illustrated embodiment has a core section 22 which is preferably a unitary molded piece of foam rubber or other foamed polymer, such as foamed urethane, which provides a resilient, yet semi-rigid, structure. The core alternatively can be chunks of such resilient material packed within cover 24. Cover 24 preferably is a water-impervious polymeric covering and is preferably nontoxic and easily washable. In the preferred embodiment, the core is a single piece of foam with the imperious polymeric covering being bonded by heat or adhesive bond. Suitable impervious covering materials include polyurethane coating. In the preferred embodiment disposed over the core cover 24 is fabric cover 26. Fabric cover 26 is preferably removable attached to the pillow 10 and is of a soft, breathable fabric, such as cotton, cotton-polyester blend or other known fabrics. Cotton or cotton-polyester blend are preferred because they are soft and also breathable. The fabric cover provides a soft, washable surface which, when in contact with the patient's skin or held close to his skin, minimizes sweating and also provides some absorption in the event of sweating. Also, the fabric cover is preferably removable so that it may be periodically cleansed. In the event of a spill, fabric cover 26 can be removed and washed, and any remaining residue can easily be wiped off of the impervious core cover.

The dimensioning of the pillow and whether one or two neck support elements are desired is a matter of choice which will vary with the size of the patient and the patient's application. The width of the pillow at the top should be sufficient to extend in front of the patient's shoulders such that the neck support elements will extend on either side of the neck of the patient toward the patient's back. The depth of the frontal section should be sufficient to impart sufficient rigidity in the pillow to maintain the body in an upright posture and support the chin. The frontal portion can be shaped in any desired shape, and in the embodiment shown, the lower portion 16 is of less width than the upper portion, providing two ledges 28 on either side of lower portion 16. This shape is desirable because a strap may be passed around lower portion 16 and under ledges 28 and taken around the patient and behind the back of a wheelchair to secure the pillow, patient and wheelchair together. The ledges assist in maintaining the pillow's position vertically and horizontally on the patient. The width, height and depth of the neck support element is a matter of choice to provide the appropriate degree of support to the head and neck. Generally, it is preferable for the support element 20 to have a height such that it will reach from the patient's shoulder to a location just below the patient's ear. The support element will have a depth sufficient to take it from the front section of the support pillow to the rear of the patient's neck, or further if desired, and will have sufficient width to provide sufficient structural support to hold the head upright without substantial displacement of the neck support element. As one will appreciate, the thickness of the particular parts depends upon the size of the pillow, the foam material used to structure the material and the resiliency of the foam utilized to construct the pillow. A stiffer foam can be used in smaller dimensions, whereas a more compressible foam will require thick portions, because the stiffer foam will provide greater support. It has been found for a pillow designed for use with a child approximately 55 pounds and 54 inches in height that a pillow with a depth of the frontal portion of 2¼ inches, a height of 15 inches and a width of 12 inches with a neck support element being 2¼ inches in width, 2¼ inches in height and 4½ inches in depth was useful. This pillow was constructed from close-celled polyurethane type of foam.

Figure 2:
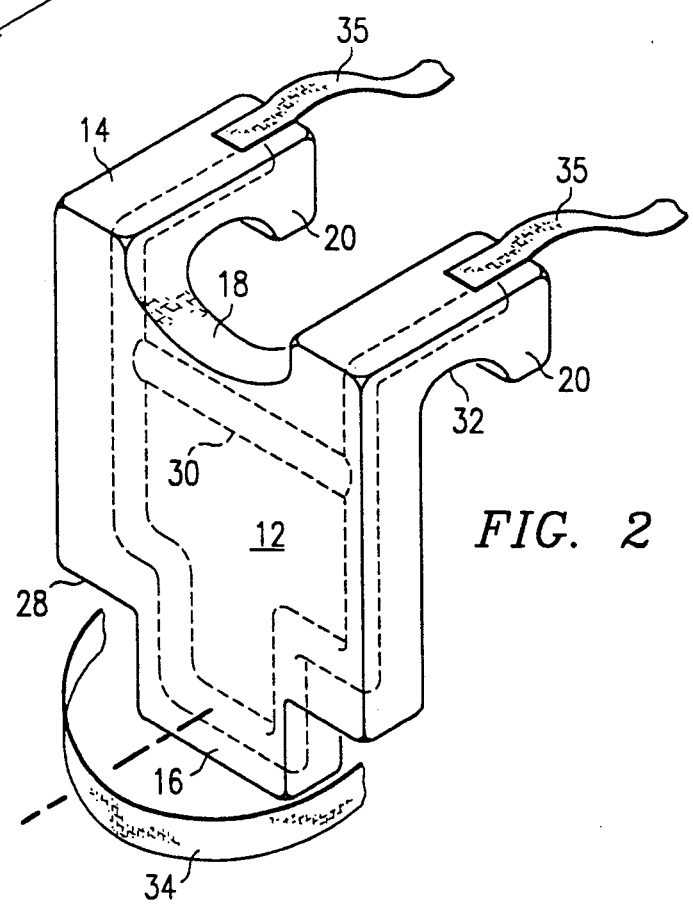
FIG. 2 is an isometric view of a second embodiment of the present invention with an internal framework shown in phantom.

FIG. 2 illustrates a pillow like that in FIG. 1 of unitary construction. Like numbers in FIG. 2 refer to like numbered items as discussed in reference to FIG. 1. In the embodiment shown in FIG. 2, two neck support elements 20 are utilized. Further, in this embodiment, shown in phantom is an internal frame structure 30. This internal frame may be of any suitable material, such as aluminum, rigid plastic, steel, wood, etc. Preferably, the inner frame is of a lightweight rigid material or substantially rigid material. In this embodiment, the core material can be foamed around the tubing to provide the overall shape of the pillow, and again, the pillow is preferably covered with the impervious core cover and also a removable fabric cover. As shown in FIG. 2, neck support elements 20 may have a bottom portion contoured to hook over a patient's shoulder, so that the front and back of the neck support element extend lower than the bottom of the mid-portion of the neck support elements. In this embodiment, the neck support elements will extend beyond the back of the patient's neck in order to hook over the patient's shoulder. For most patients, it will be desirable that the neck support elements do not extend behind the back. Also shown in FIG. 2 is strap 34, which is shown in an exploded view. The strap may be affixed to the bottom portion 16 of the support pillow to form an integral portion of the pillow. Additional straps can also be provided. For example, straps 35 can be affixed to the rear of the neck support elements.

FIGS. 3, 4 and 5 illustrate a third embodiment of the support pillow which provides a pillow which is more adjustable to meet the needs of different patients or growing patients. In these figures, like numbers refer to like elements. FIG. 3 shows a frontal view of the support 50. The pillow has a frame 52. This frame may be constructed of any substantially rigid material, such as described above. The preferred material is aluminum. A rigid frame is preferred since it does allow for a pillow which uses less foam, so that the pillow is not as bulky. It also provides better support in maintaining an erect posture for the patient. Attached to the frame are straps 54. One or more straps may be used. These straps are secured to the pillow by suitable means, such as screws 56. In the embodiment shown, a number of additional screw holes 58 are provided in the frame. These permit the locations of the straps to be adjusted to suit individual patients, and also to provide variation of the strap locations on the patients to prevent or minimize irritation from prolonged use of the straps in one location. Other suitable connecting means can be employed, such as hooks and loop closures, e.g., Velcro, or D-loops. The straps can be provided with suitable closures or buckles (not shown) or can be tied together.

Formed about the frame 52 is a resilient main pillow frontal element 60. In the preferred embodiment, the front portion of pillow 60 does not cover that portion of the frame where the screw holes 58 appear, to permit easy adjustment of the straps. The rear portion of pillow 60 extends beyond the frame. This is preferable to provide protection to the patient against patients impacting the rear side of the rigid frame with their hands while it is being worn. The main element 60 is preferably covered with an impervious covering, such as polyurethane covering 64. The upper front element 62 of the pillow in the preferred embodiment is of a different material than the main body 60; however, they can both be of the same material. In the preferred embodiment, the material utilized on the upper portion 62 is sold under the trade name "CONSERFOAM" by Wilshire Foam Products Inc., a foam utilized by NASA which is extremely comfortable and will conform to each individual's chin and will slowly regain its shape when pressure is relieved. Again, this foam is preferably covered with an impervious layer 66. Of course, the layers 66 and 64 may form one continuous layer, but for convenience have been illustrated as separate layers for each component 60 and 62. As illustrated, frame 52 can be rectangular aluminum hollow channels. At the top of the frame 52 are openings 68 whereby the frame 70 of the shoulder support element 72 may be inserted into the top of frame 52 such that an extension 74 of frame 70 will mate with the top of frame 52 and secure the neck support element 72 to the top of the frame. The neck support removed from the front section is shown in phantom as 71. The means for attaching the neck support is a male-/female connector. Preferably, the female portion is carried on the front section and the female section carried in the neck support. Further, as illustrated, it is preferred that the connection be constructed to prevent rotation of the neck support element about the front section. This can be done with mating rectangular sections. Additionally or alternatively, securing means can be provided if desired in the form of hook and loop layers 76 and 78, commonly known as Velcro. Also in the preferred embodiment are additional frame sections 80 which are adopted to receive the neck support element and serve as an alternative location for the attachment of the neck support elements. One or more additional frame sections 80 may be added. These frame members are open at their tops 82. Thus, the positioning of the neck support element 72 can be varied by inserting frame extensions 78 of the neck support element 72 into the desired receptacle of frame 52 or one of the extensions 80. Thus, the support pillow is adaptable to different sized patients or as a child grows.

As shown in FIG. 5, the support pillow 50 may also be provided with extension elements 90 and 92 for the bottom portion of the pillow. These extension elements can be affixed using hook and loop layers 94 and 96 (commonly sold under the trademark "VELCRO®", or with a securing member 98 which can be affixed to the bottom of frame 52 with screws through holes 100. Thus, the height of the pillow may be varied to suit different patients or to accommodate growth of a child. It has been found preferable for the pillow to be of sufficient height that the bottom portion can rest on the patient's legs when sitting when the patient's chin is in contact with the chin support section.

The foam used for the core of the body and neck support element can be any suitable foam, such as cross-linked or noncross-linked polyethylene fine closed-cell foam, expanded polyvinyl chloride foam, closed-cell polyvinylchloride/nitrile blend, synthetic sponge rubber or polyurethane foam. Preferably, the foam has a density in the range of 1.5 to 6.0 pounds per cubic foot, and most preferably, 1.5 to 3.0 pounds per cubic foot. The compression resistance of at least 25% deflection in pounds per square inch is preferably to the range of about 3 to 9 p.s.i., and most preferably from 5 to 7 p.s.i. Other foam may be used depending on the desires of particular patients.

The present invention provides many benefits to the patient. The individual can gain self-respect and more normally participate in functions, as their vision is directed outward and not focused on the floor by a drooping neck or on the ceiling by being confined to bed. Because the support allows for the proper drainage of the sinus passage and the throat, it decreases respiratory problems. The pillow provides a support system which is useful with conventional wheelchairs without modification of the wheelchair. The support also maintains the patient's posture. In a child, for example, suffering from muscular dystrophy, maintaining the proper posture is important to assure that skeletal growth is proper. Further, the pillow can provide support to the shoulders by placing straps high on the front of the frame. In the preferred embodiment, the pillow can be adjusted to meet particular users' needs and also to accommodate growth of child users. The pillow is of great benefit to individuals who suffer multiple handicaps and require proper positioning to function comfortable and to the best of their abilities.

I claim:
1. A support pillow comprising:
  (a) a substantially planar frontal portion having a top and a bottom formed from a resilient foam, said foam having a density in the range of 1.5 to 6.0 pounds per cubic foot and a resistance to compression of at least 15% deflection in the range of 3 to 9 pounds per square inch of pressure, said frontal portion having a sufficient length and width to extend between the shoulders and support the chin and head, wherein a portion of said top is configured as a chin rest dimensioned to hold the head in a substantially upright position with a mid-point lower than the two outer ends of said top, said outer ends being higher than the shoulders; and
  (b) at least one neck support element formed from a resilient foam, said foam having a density in the range of 1.5 to 6.0 pounds per cubic foot and a resistance to compression of at least 25% deflection in the range of 3 to 9 pounds per square inch of pressure, extending from the top of said frontal portion adjacent to said chin support section, said neck support element extending rearwardly from said frontal portion and being of sufficient height to extend from the top of the shoulder up along a portion of the neck to a level slightly below ear level; said neck support having sufficient rigidity to support the head in a substantially upright position.

2. The pillow of claim 1 wherein the front section and neck support elements are formed from a unitary molding.

3. The pillow of claim 1 wherein said frontal section and neck support elements are covered with a water-impervious covering.

4. The pillow of claim 1 further comprising a removable fabric cover.

5. The pillow of claim 1 further comprising an internal frame.

6. The support pillow of claim 1 further comprising a frame forming a portion of said planar frontal portion to which the resilient foam is attached.

7. The support pillow of claim 1 further comprising a frame member to which the resilient foam of the neck support element is attached.

8. An adjustable support pillow comprising:
  (a) a frame defining a predetermined shape; and
  (b) resilient foam molded about said frame so as to define a chin rest dimensioned to hold the head in a substantially upright position at the upper portion of said frame and to create a frontal portion of the support pillow, said foam having a density above 1.5 pounds per cubic foot and resistance to compression of at least 25% deflection above 3 pounds per square inch of pressure;

(c) means for removably attaching at least one neck support element to the top of said pillow adjacent to said chin rest (d) at least one neck support element attached to said frame, said neck support element extending rearwardly from the front of said frame and being dimensioned to extend from the top of the shoulder to a height slightly below ear level and having sufficient rigidity to hold the head in a substantially upright position; and (e) an impervious cover over said foam portions.

9. The apparatus of claim 8 wherein said cover is removable.

10. The apparatus of claim 9 further comprising means for removably attaching support straps to said frame.

11. The apparatus of claim 8 wherein said means for removably attaching neck support elements are male or female connectors.

12. The apparatus of claim 11 wherein said neck support elements have a male connector and said frontal portion of said pillow contains female connectors, dimensioned to removably receive said male connector.

13. An adjustable support pillow comprising:

(a) a frame defining a predetermined shape having a top and a bottom and sides, said frame having sufficient width to extend between the shoulders;

(b) a resilient foam attached to said frame so as to define a chin rest at the top of said frame for supporting the chin of a patient dimensioned to hold the chin above shoulder level such that the head is substantially upright thereby forming the frontal portion of a support pillow said foam having a density above 1.5 pounds per cubic foot and resistance to compression of at least 25% deflection above 3 pounds per square inch of pressure;

(c) attachment mechanism disposed on said frame for permitting the attachment of straps to said frame;

(d) means for removably attaching at least one neck support element to the top of said frontal portion; and (e) an impervious cover over said foam portions.

14. The adjustable support pillow of claim 13 further comprising at least one neck support element attached to said means for removably attaching, said neck element being of sufficient length to extend rearwardly along a patient's neck and being of sufficient height to extend from the shoulder along the neck for a sufficient height to support the neck and head in a substantially upright position, and having sufficient rigidity to hold the head and neck substantially upright.

15. The pillow of claim 13 further comprising attachment means at the bottom of said frontal portion for attaching extension pieces to said pillow such that the frontal portion can be lengthened.

16. The pillow of claim 15 further comprising an extension member attached to the bottom of said pillow.

17. The pillow of claim 13 wherein a plurality of means for removably attaching neck support elements are located along the top portion of said frontal portion to permit adjustment of the placement of one or more neck support elements.

18. The support pillow of claim 13 further comprising a neck support frame member to which a resilient foam is attached to form the neck support element.

* * * * *

UNITED STATES PATENT AND TRADEMARK OFFICE
CERTIFICATE OF CORRECTION

PATENT NO. : 5,261,420

DATED : November 16, 1993

INVENTOR(S) : Grillo

It is certified that error appears in the above-identified patent and that said Letters Patent is hereby corrected as shown below:

Col. 6, line 19, delete "15%" and substitute therefor --25%--.

Signed and Sealed this

Thirty-first Day of May, 1994

Attest:

BRUCE LEHMAN

Attesting Officer   Commissioner of Patents and Trademarks